United States Patent [19]
Pfolsgraf et al.

[11] Patent Number: 5,312,362
[45] Date of Patent: May 17, 1994

[54] SEAL FOR A CANNULA ASSEMBLY

[75] Inventors: Lanis P. Pfolsgraf, Oconomowoc; Gene T. Kyburz, Pardeeville, both of Wis.

[73] Assignee: Owens Precision Systems, Inc., Oak Creek, Wis.

[21] Appl. No.: 13,763

[22] Filed: Feb. 4, 1993

[51] Int. Cl.⁵ ............................................. A61M 5/178
[52] U.S. Cl. ...................... 604/167; 604/256; 251/149.1; 137/849
[58] Field of Search ............... 604/164, 167, 169, 264, 604/249, 256, 283; 137/849; 251/149.1, 149.2, 149.9

[56] References Cited

U.S. PATENT DOCUMENTS

| | | | |
|---|---|---|---|
| 3,853,127 | 12/1974 | Spademan . | |
| 3,970,089 | 7/1976 | Saice . | |
| 3,989,049 | 11/1976 | Yoon . | |
| 3,994,287 | 11/1976 | Turp et al. . | |
| 4,000,739 | 1/1977 | Stevens . | |
| 4,013,080 | 3/1977 | Froning | 604/165 |
| 4,079,738 | 3/1978 | Dunn et al. . | |
| 4,177,814 | 12/1979 | Knepshield . | |
| 4,261,357 | 4/1981 | Kontos | 604/167 |
| 4,430,081 | 2/1984 | Timmermans | 604/167 |
| 4,655,752 | 4/1987 | Honkanen et al. | 604/167 |
| 4,809,679 | 3/1989 | Shimonaka et al. | 604/167 |
| 4,909,798 | 3/1990 | Fleischhacker | 604/167 |
| 4,966,588 | 10/1990 | Rayman et al. | 604/165 |
| 5,009,391 | 4/1991 | Steigerwald | 604/167 |
| 5,009,643 | 4/1991 | Reich et al. | 604/167 |
| 5,041,095 | 8/1991 | Littrell | 604/167 |
| 5,092,846 | 3/1992 | Nishijima | 604/165 |
| 5,098,393 | 3/1992 | Amplatz et al. | 604/167 |
| 5,104,383 | 4/1992 | Shichman | 604/167 |
| 5,114,408 | 5/1992 | Fleischhaker | 604/167 |
| 5,122,122 | 6/1992 | Allgood | 604/174 |
| 5,141,498 | 8/1992 | Christian | 604/167 |
| 5,180,373 | 1/1993 | Green et al. | 604/167 |

FOREIGN PATENT DOCUMENTS 89304254 12/1989 European Pat. Off. .

*Primary Examiner*—John G. Weiss
*Attorney, Agent, or Firm*—Whyte Hirshboeck Dudek

[57] ABSTRACT

A self-sealing cannula assembly for maintaining pressure in a body cavity during insufflatory surgery. A cap made of elastomeric material is fitted to an enlarged portion of a cannula and has means for simultaneous sealing and fastening the cap to the cannula. The endwall of the cap may be apertured to permit entry and exit of a trocar or other surgical instrument without interruption of the seal. Another embodiment provides an elastomeric adaptor cap arranged to be fitted to the exterior circumference of the above-mentioned cap for temporary insertion and withdrawal of instruments of relatively small diameter without removal of the original cap.

12 Claims, 2 Drawing Sheets

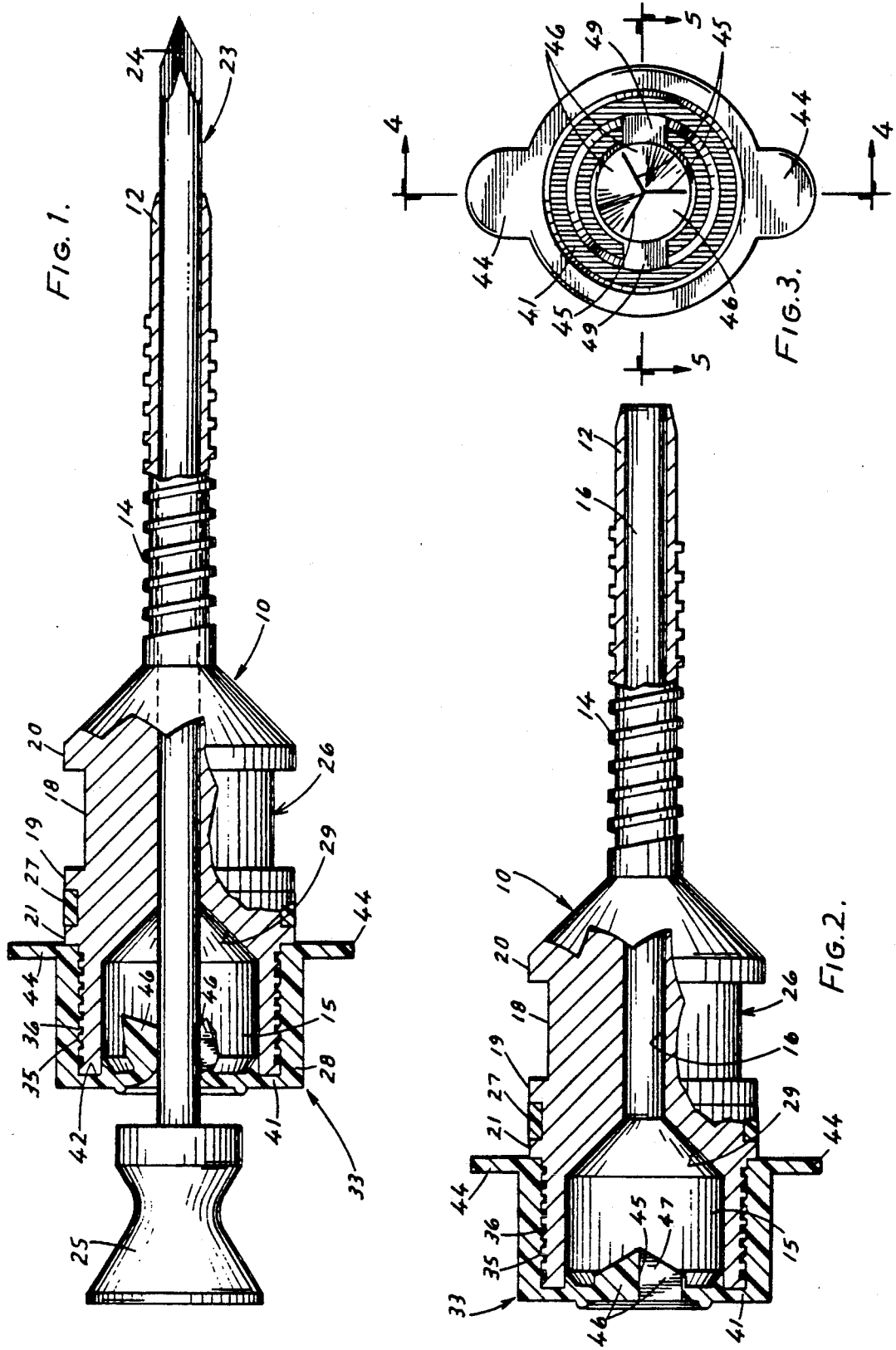

SEAL FOR A CANNULA ASSEMBLY

BACKGROUND OF THE INVENTION

1. Field of the Invention

The present invention relates to a self-sealing cannula assembly used in insufflatory surgery.

2. Background of the Invention

Various types of cannula assemblies have been provided with valves for maintaining a certain gas pressure in a body cavity during insufflatory surgery. Insufflatory surgery involves filling a body cavity with pressurized gas to maintain the cavity under a certain predetermined pressure. A conventional technique of performing the surgery is to first puncture the skin in a predetermined region of the body cavity with a needle including a stylet, and introducing an insufflatory gas into the body cavity.

A trocar is inserted into the bore of the cannula with a sharpened portion extending from the end of the cannula. The protruding end of the trocar is used to enable the end of the cannula to enter the body cavity through an incision made by the trocar in a different locality of the pressurized body cavity. The trocar may then be removed from the cannula. Surgical instruments may be inserted through the cannula to permit required endoscopic procedures. Because the body cavity is under pressure, escapement of the insufflatory gas must be prevented during insertion of the instruments and while the surgical procedure is being performed.

The prior art contains various types of cannula assemblies provided with valves for maintaining gas pressure in the body cavity when the trocar or other surgical instruments are inserted and removed from the cannula.

Of primary interest to the present invention is an assembly disclosed in U.S. Pat. No. 4,177,814, wherein there is disclosed a self-sealing cannula which maintains insufflation pressure in a body cavity by means of a slotted elastomeric valve positioned in a valve seat with the slots disposed over the cannula valve passage. Separate means are provided to compress the valve against a valve seat to seal the slot or slots.

Other patented cannula assemblies designed to maintain gas pressure within a body cavity include U.S. Pat. No. 3,853,127, which discloses a certain type of perforation formed in an elastic sealing member.

U.S. Pat. No. 3,994,287 discloses an assembly wherein gas pressure is maintained by means of a flexible ring having an aperture positioned within an annular valve seat. A collar is placed over the ring to seal the sidewalls of the valve seat. The disclosed assembly unfortunately loses it seal when the surgeon removes the instrument, and other sealing means must be provided to maintain gas pressure.

Another cannula assembly is disclosed in U.S. Pat. No. 3,989,049, wherein a trumpet valve is used to maintain pressure. Here, the trumpet valve must be manually regulated by the surgeon while removing the trocar and replacing it with another instrument, such as a laparoscope.

U.S. Pat. No. 5,041,095 discloses a hemostasis valve to prevent blood leakage. This valve assembly utilizes a snap-on cap which houses at least a pair of separate discs, each having slots for receiving a catheter to prevent backflow of blood.

Another device for introducing a catheter into a body for diagnosis or treatment, as in the case of a vascular balloon catheter, a catheter for angiography or other need for insertion into a blood vessel is shown and described in U.S. Pat. No. 5,092,846.

A seal for use with a cannula assembly is disclosed in U.S. Pat. No. 5,104,383. This disclosure is directed principally to a stabilizer plate to limit the eccentric movement of an instrument relative to the seal, which may inadvertently release the gaseous seal.

A hemostasis valve formed of a longitudinally extended valve housing is disclosed in U.S. Pat. No. 5,114,408. An apertured cap is provided for enclosing a first opening of the housing. The cap permits insertion of a catheter.

U.S. Pat. No. 5,122,122 discloses a trocar sleeve provided in a relatively complicated assembly requiring an expanded end of the trocar sleeve in abutting relationship with the inner surface of the abdominal cavity.

A particular configuration of slits formed in a self-sealing gasket for a catheter was disclosed in European Patent Publication 0 344 907 A2.

It is an object of the present invention to provide a cannula assembly having positive sealing during entry, use and substitution of surgical instruments and removal of a surgical instruments during the performance of a surgical procedure.

It is among the various objects of the invention to provide a single cap of an elastomeric material, such as silicone, in which the inner circumferential wall surface is provided with a plurality of axially spaced grooves adapted to be received by interfitting, axially spaced lands formed in the outer circumferential wall of an enlarged cuplike portion of a cannula.

It is another object of the present invention to provide a single sealing member for a cannula assembly to thereby eliminate the need for an additional compressing retainer member requiring machined threads and other machined surfaces to receive and compress a sealing valve to thereby insure sealing requirements in prior devices.

It is a further object of this invention to provide a cannula configuration which permits several variations of elastomeric gas-sealing caps or valves adaptable for use with inserted instruments of varying diameters and configurations.

A still further object of this invention is to provide an additional elastomeric adaptor cap to be received by the external surface of a first self-sealing elastomeric cap, whereby the outer cap has a sealing opening for an instrument of relatively small diameter and without requiring removal of the first cap during surgery and which will maintain the seal of the cannula assembly.

SUMMARY OF THE INVENTION

The objects are accomplished according to the present invention by the provision of a self-sealing cannula assembly including a cannula with an elongated sleeve defining a through bore for receiving a trocar for initially piercing into an operative body cavity which is to be maintained under gas pressure during a surgical procedure. The trocar may be removed through an apertured elastomeric valve or cap enclosing the open end of a cuplike portion of the cannula having an enlarged diameter to provide inter alia a fingergrip surface, the outer surface of which cuplike portion includes a series of axially spaced alternating lands and grooves. The grooves and lands are adapted to receive matching lands and grooves formed on the inner surface of the elastomeric cap for removably fastening and sealing the cap to the enlarged cannula portion. An endwall of the cap may be apertured to include a series of Y-shaped slots extending radially from the axis of the cap for receiving the trocar and permitting its removal and insertion of other surgical instruments during an insufflatory surgical procedure without loss of gas pressure.

Another embodiment of the improved elastomeric cap of this invention may be formed without an aperture endwall and may be pierced simultaneously by a sharp-pointed trocar as it is inserted in the cannula passage, or the aperture may be of a specific diameter to specifically accommodate an instrument of a particular diameter, i.e. 5 mm, 6 mm and 10/12 mm diameter instruments being common. In practice, the non apertured cap may accommodate relatively small instruments, such as a 5 mm needle, whereas 8 mm and 10/12 mm diameter instruments will ordinarily require an aperture, such as the aforementioned Y-slitted configuration.

Another embodiment of the invention takes the form of an elastomeric adaptor cap formed with an inner diameter arranged to fit relatively tightly to the outer diameter of the first-mentioned elastomeric cap. The adaptor cap permits a surgeon, who has begun the surgery with the original cap with, for instance, the slotted aperture for accommodating a 12 mm instrument, and who during the course of surgery, decides to temporarily use a 5 mm instrument. To prevent gas leakage while using the smaller diameter instrument, a non-apertured adaptor cap may be fitted over the 12 mm cap previously seated on the cannula for receipt of the smaller instrument. The adaptor cap may be removed from the first-mentioned cap, along with the 5 mm instrument, with the seal remaining intact. Prior procedures require the surgeon to either (1) pull off the 12 mm cap from the cannula and insert a 5 mm cap with consequent loss of gas pressure, or, (2) insert a special 12 mm diameter tube into the 12 mm slotted opening and then insert a 5 mm instrument therein.

These and other objects and features of the present invention will become more fully apparent from the following description and appended claims taken in connection with accompanying drawings.

BRIEF DESCRIPTION OF THE DRAWINGS

In the Drawings

FIG. 1 is a side elevation of a self-sealing cannula in accordance with the invention, shown with an associated trocar in its extended position and with certain parts being broken away and shown in longitudinal section to illustrate certain features of the present invention;

FIG. 2 is another side elevation, similar to FIG. 1, with the associated trocar removed from the cannula and also with certain parts being broken away and shown in longitudinal cross-section;

FIG. 3 is a bottom view looking interiorly of the elastomeric cap of the present invention when the cap has been removed from the cannula;

DETAILED DESCRIPTION OF PREFERRED EMBODIMENT

Figure 4:
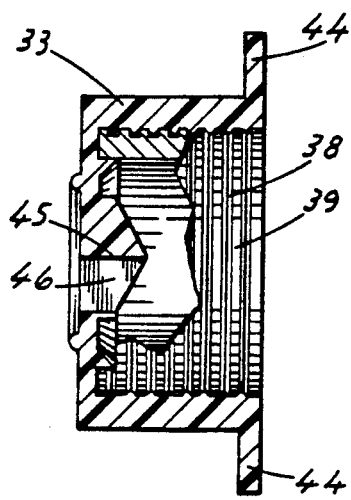
FIG. 4 is a longitudinal cross-sectional view of the cap removed from the cannula and taken along lines 4—4 of FIG. 3.

With reference to the drawings and especially to FIGS. 1-5, inclusive, there is shown a self-sealing cannula assembly in accordance with the present invention. The cannula comprises a body 10 and an elongated sleeve 12. The sleeve 12 is connected to the body 10 by conventional means, such as threading, force-fit with or without crimping, or by means of other suitable conventional procedures. The sleeve 12 is preferably formed with axially spaced threads or other radially extending projections 14 for retention of the cannula when inserted into a body cavity.

The body 10 includes a bore 15 which extends longitudinally through the body. The sleeve 14 and the tapered bore 15 communicate to define a cannula passage 16 extending through the device. The material from which the body 10 may be made may be stainless steel, or of a high temperature thermoplastic or thermoset resin, or any material which will be acceptable for sterilization by gas, autoclave or cool sterilization.

A fingergrip portion 18 of expanded diameter is defined by axially spaced, radial flanges 19 and 20 to facilitate easy grasping and manipulation by an operating surgeon. Seated between the flange 19 and a coaxially spaced auxiliary flange 21 is an annular band of color-coded material, which may comprise a silicone coating of a color chosen to match the color of a resilient cap 33 as will be described hereinbelow.

The passage 16 is arranged to receive the shaft portion 22 of a trocar 23 having a sharp distal end portion 24 and terminating into a handle 25. It will be obvious that the cannula assembly may be utilized with various types of pointed or blunted trocars, and is arranged for receiving various surgical instruments upon removal of the trocar 23 from the cannula body 10.

The body 10 of the cannula assembly is formed at its rearward end 26 to provide an enlarged, cuplike chamber 28 of relatively enlarged diameter and tapered surface 29 which tapers forwardly to terminate in the internal passage 16 of the cannula body 10. This interior chamber 28 provides a cavity for receiving inwardly projecting portions of an elastomeric apertured a slotted cap or valve member 33 arranged to enclose the open end of the chamber 28. With particular reference to the cap 33 and the enlarged rearward end portion 26 of the cannula body 10, it will be observed that the elastomeric cap 33 is formed to provide a self-sealing relationship with the body 10. This self-sealing relationship is accomplished by forming a series of alternating, radially extending lands 35 and grooves 36 on the outer circumference of the rearward end 26 of the cannula body 10. The axially spaced lands 35 and grooves 36 of the body 10 are arranged to received respective registering grooves 38 and lands 39 formed in the internal circumferential surfaces of the sealing cap or valve 33. The cap or valve 33 is formed of an elastomeric material, such as silicone, which permits a relatively "snap fit" when the resilient or elastomeric cap 33 is pushed inwardly of the body 10 until the interior flat surface 42 of the cap 33 endwall 41 abuts the outermost marginal edge surface of the body 10. The cannula body 10 with the cap 33 seated thereon provides a tight gas seal. Radially extending, oppositely disposed, ear portions 44 are integrally formed with and extend radially from the cap 33 to provide fingergrips for ease in insertion and removal of the cap 33 from the cannula body 10.

Since cannula assemblies are conventionally manufactured and sold in various sizes, the present invention further contemplates the provision of color-coding means to assist in matching a cannula body 10 of given size with a cap of matching size. As illustrated in the veiws of FIGS. 1 and 2, there is provided an area defined by axially spaced flanges 19 and 21. A layer or band 27 of a material selected to match the color of a cap 33 having a diameter matching that of the enlarged rearwall portion of the body 10. Thus, during a surgical procedure there may be cannula assemblies chosen by the surgeon to receive trocars or other instrument of a particular diameter which may vary in size depending on the instrument used. The color-coded layer or band 27 will readily assist in selecting a cap 33 of the same color coding to insure a proper fit between the matching components. The band or layer 27 may be formed by depositing a layer of silicone of selected color between the flanges 19 and 21. Other color-coding means, including adhesively affixed separately fabricated color-coded bands may also be used without departing from the invention described and claimed herein.

Figure 5:
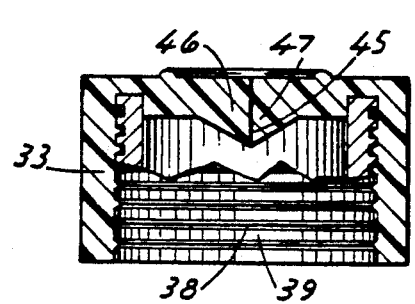
FIG. 5 is a longitudinal cross-section view of the cap removed from the cannula and taken along lines 5—5 of FIG. 3.

With particular reference to FIGS. 3-5, inclusive, it will be noted that, for receipt of the trocar 23, as illustrated in FIG. 1, and of later inserted surgical instruments (not shown), upon removal of the trocar 23, the valve or sealing cap 33 may be apertured and formed with Y-shaped slits 45. The slits 45 define valve flap areas 46, which are relatively conventional and are shown by the prior art. The flap areas 46 are further defined by an inwardly projecting convex, pyramidal-like portion or area 47 for providing added strength to the endwall 41 of the cap 33. It is of particular interest that the cap 33 does not require any additional compression type fittings, but may be made as one integrally formed unit of elastomeric material, which is both resiliently flexible and self-sealing, because of the elasticity providing the tight fit between the relative lands and grooves of the body 10 and cap 33. Additional lateral strength may be provided to the endwall 41 by means of the diametrically opposed bridging portions 49 (See FIG. 3), which are integrally molded into the single piece elastomeric cap or valve 33.

It will be observed from the illustrations of FIGS. 1 and 2 that the pointed trocar 23 may be inserted in the passage 16 of the cannula body 10 with the surgeon grasping the handle 25 thereof with one hand and the fingergrip portion 18 of the body 10 with the other hand to initially pierce the patient's skin and enter into the gas-filled body cavity of the patient for assistance in inserting the cannula sleeve 12 into the initially punctured opening formed by the trocar 23. The radially extending lands 14 on the sleeve 12 of the body 10 provide additional retention of the sleeve 12 after the cannula has been inserted into the gas-filled body.

With reference to FIG. 1, it will be apparent that, during insertion of the trocar 23, the flap portions 46 will be caused to extend inwardly of the cavity 28 of the body 10. The elastomeric material of the flap portions 46 will provide the needed self-sealing characteristics for retention of the required gas pressure in the body cavity of the patient. Withdrawal of the trocar 23, leaving the cannula body devoid of any inserted instruments, as shown in FIG. 2, will permit the flap portions 46 to retract to their original configuration for maintenance of the required seal and with the cannula sleeve 12 remaining in the body cavity. Obviously, additional instruments may be inserted into the slits 45 of the body 10 for usual surgical endoscopic procedures. These instruments may be inserted and removed as needed without interruption of the desired sealing characteristics.

Figure 6:
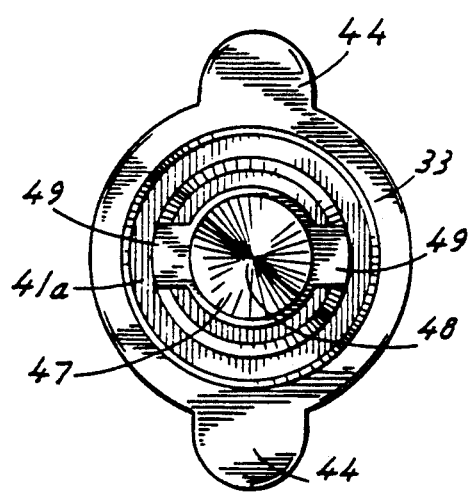
FIG. 6 is a bottom view of an elastomeric cap removed from the cannula and illustrating another embodiment of the cap formed with a relatively small, non-slitted aperture.

It will be further observed that in the embodiment described above in connection with the illustrations of FIGS. 1-5, the aperture formed by the radially arranged slits 45 are intended to accommodate relatively large diameter instruments, such as those having 10/12 mm diameters. Should the surgeon require insertion of smaller instruments, such as conventional 5 mm diameter instruments, the cap or valve 33 is preferably provided with its endwall 41 a non-slitted, but relatively small diameter aperture 48. It is conceivable that the endwall thickness may be made thin enough to permit entry of a sharply pointed, small diameter instrument through the endwall 46a as illustrated in the view of FIG. 6.

Figure 7:
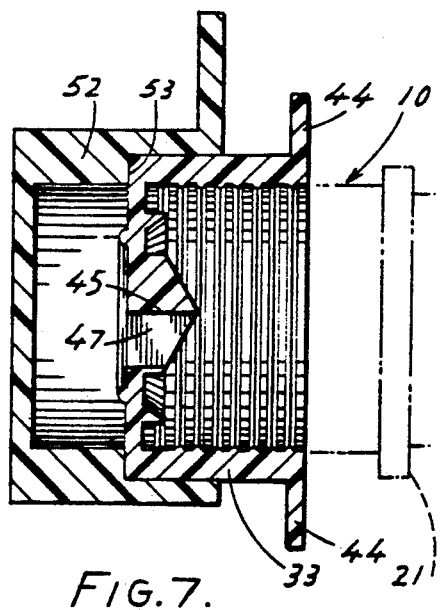
FIG. 7 is a longitudinal cross-sectional view of the elastomer cap to be fitted directly to lands and grooves formed in the outer circumference of an enlarged portion of a cannula (shown here in phantom line), and further being fitted with an adaptor cap for providing an interim seal during temporary insertion and removal of a surgical instrument of relatively small diameter into the aperture of the first-mentioned cap having a valve or slotted aperture adopted to initially receive a trocar and/or other surgical instruments of larger diameter.

With the above in mind, reference will now be had to the construction of the adaptor cap 52 for temporary use of instruments of relatively small diameter, i.e., 5 mm. There are a number of instances where a surgeon working on a insufflatory procedure may wish to use instruments of varying diameter. The present invention permits the surgeon to make an initial insertion of a cannula having a cap 33 with an aperture formed in the manner of the disclosed slits of FIGS. 1-5, and which accommodate a relatively large diameter instrument, i.e., 10/12 mm. The surgeon often discovers during the procedure the need for an instrument of small diameter to be inserted, and it will be apparent that the Y-shaped slits of the embodiment of FIGS. 1-5 might not readily provide the required seal when the larger instrument has been removed and the temporary smaller-diameter instrument is inserted. In such case, it is contemplated, as shown in FIG. 7 to provide an adaptor cap 52 of elastomeric material, such as silicone, which may be temporarily fitted to the cap or valve 33 which has been previously applied and seated on the body 10 of the cannula. In such case, an adaptor cap 52 perforated or apertured to receive a small (4.5 mm) diameter instrument. The adaptor cap 52 is preferably made of the same material as the cap or valve 33, may be directly fitted in "piggy back" relationship over the exterior diameter of the cap 33, as shown in FIG. 7. A shoulder portion 53 acts as an imbutment for stopping the insertion of the cap 52 relative to the cap 33. It will also be noted that a fingergrip or ear 54 may be provided to facilitate insertion and removal of the adaptor cap 52. It is further noted that the cap 52 may be non-perforated, to receive the smaller (5 mm) instrument, which smaller instrument further projects through the Y-slits 45 of the cap 33. After the surgeon finishes his procedure using the smaller diameter instrument, both the smaller diameter instrument and the adaptor cap 52 may be removed to provide for entry of an instrument of larger diameter. The gas seal will not be broken during any of the described procedures used in connection with the assembly of FIG. 7.

It will be apparent that a self-sealing cannula assembly disclosed and claimed herein will provide many advantages over prior art sealing cannulas. In addition, the present invention further contemplates the use of an adaptor cap which will permit temporary use of surgical instruments of relatively small diameter after an initial insertion of a trocar and instruments of relatively large diameter approximating that of the trocar. No additional compressive, threaded caps used in prior art devices are necessary, and which require additional manipulation and may possibly be lost during cleaning and sterilization procedures.

We claim:

1. In a self-sealing cannula assembly for insufflatory surgical procedures, and wherein said cannula assembly comprises a cannula having an elongated sleeve defining a cannula passage for receiving surgical instruments therethrough and for penetrating into an operative body cavity to facilitate insertion and withdrawal of a surgical instrument while retaining said cannula in situ and while retaining gag pressure in said body cavity notwithstanding withdrawal of said surgical instrument, said cannula having a cuplike portion of enlarged cross-section disposed at its rearward end, said cuplike portion having an open-ended entrance defined by a marginal end surface for receiving the surgical instruments, the improvement comprising, an elastomeric cap having an endwall for enclosing said open-ended entrance of said cuplike section, said elastomeric cup having a centrally located, inwardly projecting convex area and having an inner circumference substantially conforming to the outer circumference of said cuplike portion of the cannula, said elastomeric cap further being self-retaining for seating engagement and securement with the outer circumference of said cuplike portion of the cannula to provide a gaseous seal.

2. The cannula assembly of claim 1, wherein a bridging integral support element projects inwardly from the endwall of said elastomeric cap and which radially extends from the axis of said cap to the inner circumferential wall of the cap to provide additional rigidity to the said endwall.

3. The cannula assembly of claim 1 or 2 wherein the endwall of the cap is apertured for receiving a surgical instrument.

4. The cannula assembly of claim 1, wherein the endwall of the cap includes an aperture defined by a Y-shaped slitted area for receiving a surgical instrument, the legs of said Y-shape being located in the inwardly projecting convex area and projecting radially outwardly from the axis of said convex area.

5. The cannula assembly of claim 1, wherein the endwall of said elastomeric cap includes a relatively small, non-slitted, aperture to permit a surgical instrument of relatively small diameter to initially pierce the elastomeric endwall and provide a self-seal with said instrument.

6. The cannula assembly of claim 1, wherein the elastomeric cap includes at least one laterally projecting, integrally formed, fingergrip portion for facilitating placement and removal of said cap to and from said cuplike cannula portion.

7. The cannula assembly of claim 1 further comprising color-coding means providing matching color identification to said cap and to said cannula, to thereby assist in facilely selecting a cap matching a cannula of corresponding engaging surface dimension.

8. The self-sealing cannula assembly of claim 7, wherein said cap includes at least a portion thereof of a preselected color, and at least a portion of the exposed outer surface of said cannula is color-coded to match the color of said cap.

9. The cannula assembly of claim 1 in which the endwall of the elastomeric cap abuts the marginal end surface of the cannula cuplike portion.

10. The cannula assembly of claim 1 further comprising an elastomeric adapter cap having an inner circumference corresponding to the outer circumference of the elastomeric enclosure cap and arranged to be fitted over and in sealing relationship with the enclosure cap, the adapter cap having an endwall adapted for receiving in sealing engagement a surgical instrument.

11. The cannula assembly of claim 10, wherein the adaptor cap has an integrally formed endwall having a non-slitted aperture of relatively small diameter to permit the surgical instrument of lesser diameter to pierce its own initial receptive, self-sealing opening.

12. The cannula assembly of claim 1 in which the outer circumference of said cuplike portion contains a plurality of alternately axially spaced grooves and lands that are in mated and sealing engagement with corresponding alternately axially spaced lands and grooves on the inner circumference of said elastomeric enclosure cap.

* * * * *